(12) United States Patent
Finch

(10) Patent No.: US 8,618,022 B2
(45) Date of Patent: Dec. 31, 2013

(54) PROCESS FOR PREPARING AN AQUEOUS SUSPENSION OF AN ORGANIC PESTICIDE COMPOUND

(75) Inventor: Charles W. Finch, Garner, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/383,652

(22) PCT Filed: Jul. 13, 2010

(86) PCT No.: PCT/EP2010/060072
§ 371 (c)(1),
(2), (4) Date: Jan. 12, 2012

(87) PCT Pub. No.: WO2011/006896
PCT Pub. Date: Jan. 20, 2011

(65) Prior Publication Data
US 2012/0128750 A1    May 24, 2012

Related U.S. Application Data

(60) Provisional application No. 61/225,380, filed on Jul. 14, 2009.

(51) Int. Cl.
| | |
|---|---|
| A01N 25/02 | (2006.01) |
| A01N 43/56 | (2006.01) |
| A01N 43/653 | (2006.01) |
| A01P 3/00 | (2006.01) |
| A01P 13/00 | (2006.01) |
| A01P 21/00 | (2006.01) |

(52) U.S. Cl.
USPC ........ 504/116.1; 424/405; 504/118; 504/127; 504/347; 514/383; 514/407

(58) Field of Classification Search
None
See application file for complete search history.

(56) References Cited

U.S. PATENT DOCUMENTS

| | | | |
|---|---|---|---|
| 4,571,088 A | 2/1986 | Frensch et al. | |
| 6,541,426 B1 * | 4/2003 | Kostansek et al. | 504/341 |
| 2002/0128154 A1 * | 9/2002 | Fafchamps et al. | 504/347 |
| 2006/0116290 A1 * | 6/2006 | Heming et al. | 504/360 |
| 2008/0234350 A1 * | 9/2008 | Ziegler et al. | 514/407 |
| 2010/0179198 A1 | 7/2010 | Mertoglu et al. | |

FOREIGN PATENT DOCUMENTS

| | | |
|---|---|---|
| EP | 0 145 879 | 1/1989 |
| EP | 0 249 075 | 4/1991 |
| EP | 1 060 667 | 12/2000 |
| WO | WO 01/80828 | 11/2001 |
| WO | WO 2006/136357 | 12/2006 |
| WO | WO 2009/007328 | 1/2009 |

OTHER PUBLICATIONS

International Search Report, PCT/EP2010/060072, May 5, 2011.
International Preliminary Report on Patentability, PCT/EP2010/060072, Nov. 14, 2011.

* cited by examiner

Primary Examiner — Frederick Krass
Assistant Examiner — Michael P Cohen
(74) Attorney, Agent, or Firm — Brinks Gilson and Lione

(57) ABSTRACT

The present invention relates to a process for preparing an aqueous suspension of an organic pesticide compound, which has a solubility in water of not more than 2 g/l at 20° C. and a melting point of not more than 110° C. and which is capable of forming at least one crystalline modification, wherein the organic pesticide compound is present in the form of essentially crystalline particles, which process comprises: a) providing an aqueous emulsion of the organic pesticide compound, wherein the organic pesticide compound is present in the form droplets of an amorphous form of the organic pesticide compound, and b) addition of an aqueous suspension of said organic pesticide compound, wherein the organic pesticide compound is present in the form of essentially crystalline particles, wherein the addition in step b) is performed at a temperature below the melting temperature of the crystalline form of the organic pesticide compound.

20 Claims, No Drawings

PROCESS FOR PREPARING AN AQUEOUS SUSPENSION OF AN ORGANIC PESTICIDE COMPOUND

This application is a National Stage application of International Application No. PCT/EP2010/060072 filed Jul. 13, 2010, which claims the benefit of U.S. Provisional Application No. 61/225,380, filed Jul. 14, 2009, the entire contents of which are hereby incorporated herein by reference.

The present invention relates to a process for preparing an aqueous suspension of an organic pesticide compound, which has a solubility in water of not more than 2 g/l at 20° C. and a melting point of not more than 110° C. and which is capable of forming at least one crystalline modification, wherein the organic pesticide compound is present in the form of essentially crystalline particles.

Organic pesticide compounds having a low water solubility, i.e. a solubility in water at 20° C./1013 mbar of not more than 2 g per litre, are frequently formulated as aqueous suspension concentrates, also referred to as SC's (or in case of seed treatment formulations as FS formulation, or simply, FS). In the SC's, and likewise in the FS formulations, the pesticide is present in the form of finely dispersed particles which are suspended in the aqueous liquid phase, which, besides water, usually contains at least one surfactant for stabilizing the pesticide particles and which may contain further formulation additives such as rheology modifiers, biocides, dyes, defoamers (antifoam agents) and anti-freeze agents. Principally, SC's can be easily diluted with water and thus provide an easy-to-handle way of application of the pesticide in the field. Moreover, SC's and FS's generally contain only small amounts of or even no organic volatiles and thus are preferred for environmental reasons.

Despite the aforementioned advantages associated with the usage of SC's and FS's, there is a number of problems known to the skilled person which are sometimes encountered with SC's and FS's as a result of settling during prolonged storage or storage at elevated temperatures, the resistance of settled particles to re-suspension and the formation of crystalline material upon storage. As a consequence, the formulations may be difficult to handle and the bioefficacy may be inconsistent.

When low melting organic pesticides are formulated as an SC one may encounter difficulties during preparation. SC's and FS's are generally prepared by suspending one or more organic pesticide compounds in water containing suitable surfactants and optionally further formulation additives and comminution of the suspended pesticide particles to the desired particle size. However, this method principally requires the organic pesticide compound to be in a solid state, preferably in a crystalline state, as the organic pesticide may clog the milling apparatus. For low melting pesticides the preparation of solid, in particular crystalline, material is often difficult. Moreover, the pesticide may melt during comminution because of the mechanical energy introduced by the comminution thereby causing clogging of the milling apparatus.

It has been severally suggested to prepare aqueous suspension concentrates of low-melting, water insoluble organic compounds by a melt-emulsification process. In the melt-emulsification process the molten organic compound is emulsified in the aqueous phase by applying high shear to the mixture which is then quenched. The melt-emulsification generally leads to aqueous suspensions or emulsions wherein the suspended/emulsified active ingredient particles are present in the form of droplets of a supercooled melt.

EP-A 249075 discloses a process for the preparation of an aqueous suspension concentrate formulation of the low melting pesticide pendimethalin, which process comprises emulsifying molten pendimethalin in an aqueous solution containing surfactants and antifoam, cooling the emulsion to solidify the pendimethalin droplets and milling the thus obtained suspension to the desired particle size of the pendimethalin particles.

EP-A 145 879 discloses a process for the preparation of aqueous suspensions of pesticide compounds, where the molten pesticide compound is metered into a cool jet of an aqueous solution of formulation additives. However, this process is limited to pesticide compounds having a melting-point significantly above 70° C.

EP-A 1060667 discloses a process for preparing aqueous suspension concentrates of water-insoluble crystalline actives, where a stream of the molten active is combined under high shear conditions in a mixing chamber with an aqueous solvent stream, thereby emulsifying the molten active, where the residence time in the mixing chamber is chosen that the emulsion cools below the melting point of the active and the active particles solidify before leaving the mixing chamber. The process, however, is limited to pesticide compounds which rapidly crystallize upon cooling.

Although these processes principally allow the preparation of aqueous suspension concentrates of water insoluble pesticide compounds, they have several limitations or disadvantages. For example, the obtained suspension concentrates might be of limited stability, in particular when the pesticide compound has a low melting point and/or shows a slow crystallization rate upon cooling. This is, because the pesticide compound particles might undergo uncontrolled particle growth due to "Ostwald's ripening" as the residual solubility of the pesticide in the aqueous suspension medium will be sufficient to allow crystallization processes such as crystallization of amorphous material or phase change of allotropic forms if the pesticide is capable of forming polymorphs. These problems will become pronounced when the suspension concentrate is stocked at elevated and/or changing temperatures.

Pyraclostrobin (IUPAC: methyl {2-[1-(4-chlorophenyl)pyrazol-3-yloxymethyl]phenyl}-(methoxy)carbamate; CAS-No. 175013-18-0) is a low melting fungicide compound having a melting point of below 68° C. Pyraclostrobin is practically insoluble in water (solubility<2 mg/l at 20° C.) (see, for example, Herms, S., Seehaus, K., Koehle, H., and Conrath, U. (2002) Pyraclostrobin—"More than just a Fungicide" Phytomedizin 32: 17; C. D. S. Tomlin (Ed.), "The Pesticide Manual", 14$^{th}$ ed. BCPC Publications Hampshire 2006). Pyraclostrobin is known to exist in four different enantiotropic crystalline forms (modifications) I to IV, the modification IV being the thermodynamically most stable form (see WO 2006/136357). Though aqueous suspension concentrates of pyraclostrobin have been described in the art, they are difficult to prepare by conventional methods not least because of the low melting point of pyraclostrobin. Apart from that, the preparation of crystalline pyraclostrobin is currently tedious and time consuming and thus it increases the costs for preparing aqueous suspension concentrates of pyraclostrobin.

Therefore it is an object of the present invention to provide a process for preparing stable aqueous formulations in the form of aqueous suspension concentrates, which formulations comprise at least one organic pesticide compounds having no or only limited water solubility and having a low melting point. The process should overcome the disadvantages of prior art and the process should allow the preparation of stable suspension concentrates of pesticide compounds having a low melting point and being capable of forming crystalline material. The process should be particularly suitable for preparing stable aqueous suspension concentrates containing pyraclostrobin, in particular of form IV of pyraclostrobin.

It has now been found that these and further objectives are met by a process for preparing an aqueous suspension of an organic pesticide compound, which has a solubility in water of not more than 2 g/l at 20° C. and a melting point of not more than 110° C. and which is capable of forming at least one crystalline modification, wherein the organic pesticide compound is present in the form of essentially crystalline particles, which process comprises the following steps a) and b):

a) providing an aqueous emulsion of the organic pesticide compound, wherein the organic pesticide compound is present in the form droplets of an amorphous form of the organic pesticide compound, and b) addition of an aqueous suspension of said organic pesticide compound, wherein the organic pesticide compound is present in the form of essentially crystalline particles, wherein the addition is performed at a temperature below the melting temperature of the crystalline form of the organic pesticide compound.

The invention is based on the surprising finding that addition of small amounts of an aqueous suspension containing essentially crystalline particles of a low melting and sparingly soluble or insoluble organic pesticide compound to an aqueous emulsion of said pesticide compound at a temperature below the melting point of said pesticide compound induces rapid and complete crystallization of the amorphous droplets of the pesticide compound contained in the aqueous emulsion without leading to the formation of coarse material, thereby yielding a stable aqueous suspension of the organic pesticide compound, wherein the organic pesticide compound is present in the form of essentially crystalline particles.

Therefore, the present invention relates to a process for preparing an aqueous suspension of an organic pesticide compound, which has a limited solubility in water, i.e. a solubility in water of not more than 2 g/l at 20° C., and a low melting point of generally not more than 110° C. and which is capable of forming at least one crystalline form, wherein the organic pesticide compound is present in the form of essentially crystalline particles, which process comprises:

a) providing an aqueous emulsion of the organic pesticide compound, wherein the organic pesticide compound is present in the form droplets of an amorphous form of the organic pesticide compound, and b) addition of an aqueous suspension of said organic pesticide compound, wherein the organic pesticide compound is present in the form of essentially crystalline particles, wherein the addition in step b) is performed at a temperature below the melting temperature of the crystalline form of the organic pesticide compound.

This process is particularly suitable for the preparation of stable aqueous suspensions of organic pesticide compounds having a limited water solubility and a low melting point and which are capable of forming at least one stable crystalline form.

Apart from that, the process of the present invention is associated with several benefits. In particular, the process of the present invention does not require the preparation of large amounts of solid crystalline material of the pesticide compound prior to formulation and thus it is less time-consuming and avoids the handling of solid crystalline material, which might be particularly problematic when the pesticide has a low melting point. Moreover, the process of the present invention does not require tedious comminution techniques as normally required in the preparation of aqueous suspension concentrates.

These stable suspensions, as obtained in step b) of the claimed process, can be used as such as an aqueous suspension concentrate formulation of said pesticide compound or can be used as a base material for further formulations, in particular for aqueous suspension concentrate formulations, which contain said low melting pesticide compound having a low melting point and limited water solubility in combination with one or more further pesticide compounds having limited water solubility of generally not more than 2 g/l at 20° C.

Therefore, the present invention also relates to a process A process for preparing an aqueous pesticide formulation in the form of an aqueous suspension concentrate containing at least one organic pesticide compound, which has a solubility in water of not more than 2 g/l at 20° C. and a melting point of not more than 110° C. and which is capable of forming at least one crystalline modification, which process comprises the preparation of an aqueous suspension of the organic pesticide compound, wherein the organic pesticide compound is present in the form of essentially crystalline particles, by a process as described herein.

"Limited water solubility" in terms of the present invention means that the pesticide compound is insoluble in water or has a solubility in water at 20° C. (1013 mbar) of not more than 3 g/l or not more than 2 g/l, in particular not more than 1 g/l, preferably not more than 0.5 g/l, especially not more than 0.1 g/l, e.g. from 0 to 2 g/l, in particular from 0.01 mg/l to 1 g/l or from 0.02 mg/l to 0.5 g/l, especially from 0.05 mg/l to 0.1 g/l. Solubility will usually be determined in deionized water at 20° C.

A "low melting point" in terms of the present invention means that the pesticide compound has a melting point of not more than 110° C., in particular not more than 95° C., preferably not more than 80° C., especially not more than 70° C., e.g. from 40 to 100° C., in particular from 45 to 90° C., preferably from 50 to 80° C. and especially from 55 to 70° C.

"Capable of forming a least one stable crystalline form" in terms of the present invention means that the pesticide compound is capable of forming a crystalline material which melts above 25° C., and which crystalline material preferably has a melting point of at least 40° C., in particular of at least 45° C., more preferably of at least 50° C. and especially of at least 55° C.

"Essentially crystalline" in terms of the present invention means that at least 90% by weight of the pesticide compound, which is present in the aqueous suspension, is in the crystalline state and that less than 10% by weight of the pesticide compound, which is present in the aqueous suspension, is not crystalline, i.e. amorphous. The degree of crystallinity can be simply determined by powder X-ray diffraction (powder XRD) of the pesticide compound, by optical microscopy (due to birefringence of the crystalline phase), in most cases also from DSC analysis (DSC=Differential Scanning calorimetry), and in some cases by IR spectrometry.

"Amorphous form" in terms of the present invention means that the pesticide compound, which is present in the aqueous emulsion, is essentially not crystalline, i.e. it contains less than 10% by weight, based on the total amount of the pesticide compound, or no traceable amounts of crystalline material. Amorphous forms include liquids forms, i.e. melt and supercooled melt and solid amorphous forms.

The process of the present invention is suitable for the preparation of stable aqueous suspensions of any organic pesticide compounds having a limited water solubility as defined above and a low melting point as given above and which are capable of forming at least one stable crystalline form. Examples of such organic pesticide compounds include but are not limited to the compounds giving in the following table:

| pesticide compound | melting point [° C.] | water solubility [1] [mg/l] |
|---|---|---|
| aldrin | 49-60 | <<1 |
| alachlor | 39.5-41.5 | 242 |
| azinphos-ethyl | 74 | 33 |
| benfluralin | 65-66.5 | <1 |
| bensultap | 82-83 | 0.7 |
| benzoximate | 73 | 30 |
| bifenthrin | 51-66 | 0.1 |
| binapacryl | 66-67 | <<0.1 |
| bromophos | 53-54 | 40 |
| bromopropylate | 77 | <5 |
| butralin | 60-61 | 1 |
| chlorphoxim | 66.5 | 2 |
| chlorpyriphos | 42-43.5 | 2 |
| fluchloralin | 42-43.5 | <1 |
| fluroxypyr | 56-57 | 0.9 |
| kresoxim-methyl | 97 | 2 |
| linuron | 93-94 | 75 |
| metazachlor | 80 | 450 |
| metconazol | 100-104.2 | 1400 |
| monolinuron | 92-94 | 735 |
| napropamide | 75 | 73 |
| nitrothal-isopropyl | 65 | 0.4 |
| pendimethalin | 54-58 | 0.3 |
| phosmet | 72.5 | 25 |
| picoxystrobin | 53-75 | 3.1 |
| pirimicarb | 90.5 | 2700 |
| picolinafen | 107-108 | <0.1 |
| pyraclostrobin | 55-64 [2] | 1.9 |
| tefluthrin | 44.6 | 0.02 |
| trifloxystrobin | 80 | 450 |

[1] water solubility in deionised water at 20° C.
[2] depending on the polymorph The process of the present invention is particularly suitable for preparing stable aqueous suspensions of pyraclostrobin. The process of the present invention is especially suitable for preparing stable aqueous suspensions of form IV of pyraclostrobin, i.e. the pyraclostrobin contained in the thus obtained aqueous suspension is essentially present as form IV (also termed modification IV) of pyraclostrobin. Thus, a particular preferred embodiment of the invention is directed to a process, where the pesticide compound contained in the emulsion of step a) is pyraclostrobin and where the crystalline pesticide compound present in the aqueous suspension that is added in step b) is essentially crystalline pyraclostrobin, in particular pyraclostrobin being essentially present as its crystalline form IV.

In terms of the present invention "essentially present as form IV (or modification IV) of pyraclostrobin" means that at least 90% of the pyraclostrobin present in the aqueous suspension concentrate is present as its crystalline form IV.

Form IV of pyraclostrobin has been described for the first time in WO 2006/136357 to which full reference is made. Form IV can be identified by its characteristic X-Ray diffraction pattern, which in an X-ray powder diffractogram at 25° C., shows at least three, in particular at least 4 and preferably all of the following reflexes:

$d=6.02\pm0.01$ Å

$d=4.78\pm0.01$ Å

$d=4.01\pm0.01$ Å

$d=3.55\pm0.01$ Å

$d=3.01\pm0.01$ Å.

Crystalline pyraclostrobin of modification IV has typically a melting point in the range from 62 to 64° C. The heat of fusion, i.e. the amount of energy required for melting the crystalline modification IV, is about 72 to 80 J/g. The melting points and heats of fusion indicated here refer to values determined by differential calorimetry (Differential Scanning calorimetry: DSC, crucible material aluminium, heating rate 5 K/min).

Studies of single crystals of modification IV show that the basic crystal structure is monoclinic and has the space group P2(1)/c. The characteristic data of the crystal structure of form IV (modification IV) are summarized in table 1:

TABLE 1

| Crystallographic data of modification IV | |
|---|---|
| Parameter | Modification IV |
| Class | Monoclinic |
| Space group | P2(1)/c |
| a | 998.5(3) pm |
| b | 4780.4(10) pm |
| c | 788.6(2) pm |
| α | 90° |
| β | 105.357(6)° |
| γ | 90° |
| Volume | 3.6301(16) nm$^3$ |
| Z | 8 |
| Density (calculated) | 1.419 g/cm$^3$ |
| R1, wR2 | 0.0651, 0.1574 | a, b, c = Length of the edges of the unit cell
α, β, γ = Angles of the unit cell
Z = Number of molecules in the unit cell The preparation of crystalline pyraclostrobin, in particular of form IV of pyraclostrobin has also been described in WO 2006/136357 to which full reference is made.

According to the process of the present invention, an aqueous emulsion of the organic pesticide compound is provided, wherein the organic pesticide compound is present in the form droplets of an amorphous form of said organic pesticide compound. Amorphous means that the pesticide compound is essentially not present in its crystalline state, which means that the amount of crystalline material in the amorphous pesticide compound is less than 10% by weight. An amorphous pesticide compound may be present e.g. in the form of a melt or a supercooled melt or an amorphous solid. The average droplet size, i.e. the volume average diameter of the droplets, is preferably in the range of from 0.5 to 10 µm, in particular in the range from 1 to 5 µm, as determined by dynamic light scattering.

The average particle diameter as referred herein, are volume average particle diameters d(0.5) or d(v, 0.5), i.e. 50 vol.-% of the particles have a diameter which is above and 50 vol.-% of the particles have a diameter which is below the mean value cited. Therefore, average particle diameters are also termed "volume median diameters". Such average particle diameters can be determined by dynamic light scattering (usually performed on diluted suspensions containing from 0.01 to 1% by weight of the active ingredient. A skilled person is familiar with these methods which are described e.g. in H. Wiese (D. Distler, Ed.), Aqueous Polymer Dispersions (Wässrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429.

The amount of pesticide compound in the emulsion will be generally in the range from 5 to 60% by weight, preferably from 10 to 50% by weight and in particular from 20 to 45% by weight, based on the total weight of the emulsion.

In addition to the pesticide compound the emulsion comprises an aqueous phase which is the dispersion medium for the pesticide compound droplets. Besides water, the aqueous phase may generally contain one or more surfactants which are suitable for stabilising the droplets in the aqueous phase.

Suitable surfactants include anionic surfactants, non-ionic surfactants and cationic surfactants or combinations thereof. The surfactants include non-polymeric surfactants which are also termed emulsifiers and polymeric surfactants, which may also termed as protective colloids. In contrast to polymeric surfactants, emulsifiers will generally have a number average molecular weight $M_N$ of not more than 1000 Dalton while polymeric surfactants will generally have a number average molecular weight $M_N$ of greater than 1000 Dalton. The nature of the surfactants is not particularly critical, e.g. they may be selected from any known dispersing agents and wetting agents. Dispersing agents are those surfactants which primarily bond to the surface of the active ingredient particles/droplets, e.g. by ionic and/or hydrophobic interaction, and which stabilize the particles in the liquid phase. Wetting agents are surfactants which primarily lower the interfacial tension between the liquid phase and the surface of the solid particles of the active ingredient (here, the pesticide compound) that are dispersed or emulsified in the aqueous phase, thereby assisting in stabilizing the particles in the aqueous phase. Wetting agents may be chosen by physical measuring of the contact angle. Particular suitable wetting agents will have a contact angle of less than 90°, in particular less than 60° (determined at 24° C./1013 mbar for a 1 M aqueous solution of the wetting agent according to DIN 53914 by the Wilhelmy method or according to extended Washburn method using a powder of the pesticide compound).

In general, the aqueous emulsions contain the at least one surfactant in amounts from 0.1 to 20% by weight, preferably from 0.5 to 15% by weight and in particular from 1 to 10% by weight, based on the total weight of the emulsion. Usually, the weight ratio of the pesticide to the surfactant is in the range of from 2:1 to 50:1, and particularly from 3:1 to 20:1.

Suitable surfactants are well known to the skilled person as are processes for the preparation thereof; they are also commercially available, e.g. under the trade names mentioned below in each case.

Preferably, the surfactant which is contained in the aqueous emulsion, comprises at least one anionic surfactant. In a very preferred embodiment of the present invention, the surfactant additionally comprises at least one non-ionic surfactant. If the aqueous emulsion contains a combination of at least one anionic surfactant and at least one non-ionic surfactant, the weight ratio of anionic surfactant and non-ionic surfactant is preferably from 1:5 to 5:1, in particular from 1:3 to 3:1. However, the emulsion may also comprise only one or more non-ionic surfactants. Preferably, the surfactant which is contained in the aqueous emulsion, comprises at least one polymeric surfactant. In a very preferred embodiment of the present invention, the surfactant additionally comprises at least one non-polymeric surfactant. If the aqueous emulsion contains a combination of at least one polymeric surfactant and at least one non-polymeric surfactant, the weight ratio of polymeric surfactant and non-polymeric surfactant is preferably from 1:5 to 5:1, in particular from 1:3 to 3:1. However, the emulsion may also comprise only one or more non-ionic surfactants.

Anionic surfactants include in particular the sodium, potassium, calcium or ammonium salts of non-polymeric anionic surfactants having an $SO_3^-$ or $PO_3^{2-}$ group, e.g.

c.1 $C_6$-$C_{22}$-alkylsulfonates such as lauryl sulfonate, isotridecylsulfonate;

c.2 $C_6$-$C_{22}$-alkylsulfates such as lauryl sulfate, isotridecylsulfate, cetylsulfate, stearylsulfate;

c.3 aryl- and $C_1$-$C_{16}$-alkylarylsulfonates such as naphthylsulfonate, mono-, di- and tri-$C_1$-$C_{16}$-alkylnaphthylsulfonates such as dibutylnaphtylsulfonate, dodecyldiphenylether sulfonate, mono-, di- and tri-$C_1$-$C_{16}$-alkylphenylsulfonates such as cumylsulfonate, octylbenzene sulfoanate, nonylbenzenesulfonate, dodecylbenzene sulfonate and tridecylbenzene sulfonate;

c.4 sulfates and sulfonates of $C_6$-$C_{22}$-fatty acids and $C_6$-$C_{22}$-fatty acid esters;

c.5 sulfates of ethoxylated $C_6$-$C_{22}$ alkanols such as sulfates of (poly)ethoxylated lauryl alcohol;

c.6 sulfates of (poly)ethoxylated $C_4$-$C_{16}$-alkylphenols and sulfates of (poly)ethoxylated di- or tristyrylphenols;

c.7 mono- and diesters of phosphorous acid, including mixtures thereof with triesters and salts thereof, in particular the esters with $C_8$-$C_{22}$-alkanols, ethoxylated $C_8$-$C_{22}$-alkanols, $C_4$-$C_{22}$-alkylphenols, (poly)ethoxylated $C_4$-$C_{22}$-alkylphenols, (poly)ethoxylated di- or tristyrylphenols; and c.8 di $C_4$-$C_{16}$ alkylesters of sulfosuccinic acid such as dioctylsulfosuccinate;

polymeric anionic surfactants having an $SO_3^-$ or $PO_3^{2-}$ group, e.g.

c.9 condensates of arylsulfonic acid, such as naphthalenesulfonic acid or phenolsulfonic acid, with formaldehyde and optionally with urea;

non-polymeric anionic surfactants having at least one carboxylate group, e.g.

c.10 fatty acids such as stearates and c.11 N—$C_6$-$C_{22}$-acylaminoacids, such as N—$C_6$-$C_{22}$-acylglutamates, N—$C_6$-$C_{22}$-acylglycinates and N—$C_6$-$C_{22}$-acylsarkosinates;

polymeric anionic surfactants having carboxylate groups, e.g.

c.12 anionic graft or comb copolymers containing poly-$C_2$-$C_4$-alkylene oxide moieties, in particular polyethylene oxide moieties PEO, grafted on a polymeric backbone and carboxylate groups attached to the polymer backbone;

c.13 anionic copolymers containing, in polymerised form, (i) $C_3$-$C_5$ monoethylenically unsaturated carboxylic acid monomers, and (ii) hydrophobic monomers having a water solubility of not more than 60 g/l at 20° C. and 1013 mbar.

Amongst anionic surfactants those of the groups c.3, c.6, c.8, c.9, c.12 and c.13 and mixtures thereof are preferred.

In the group of surfactants c.3 preference is given to mono- or di-$C_4$-$C_8$-alkylnaphthalene sulfonic acid and mono- or di-$C_4$-$C_{16}$-alkylbenzesulfonic acid and the ammonium salts, the alkaline metal salts, such as the sodium or potassium salt, and the earth alkaline metal salts, in particular the calcium salts thereof. Particularly suitable examples are Morwet® EFW (Akzo Nobel), and the like.

In the group of surfactants c.6 preference is given to the ammonium salts, alkaline metal salts and earth alkaline metal salts of sulfates of (poly)ethoxylated di- or tristyrylphenols, in particular of those having from 5 to 50, in particular 10 to 50 or 15 to 50 ethylenoxide repeating units. Particularly suitable examples of sulfates of (poly)ethoxylated di- or tristyrylphenols are Soprophor® 4D384 from Rhodia and the like.

In the group of surfactants c.7 preference is given to the ammonium salts and alkaline metal salts of phosphates of (poly)ethoxylated di- or tristyrylphenols, in particular of those having from 5 to 50, in particular 10 to 50 or 15 to 50 ethylenoxide repeating units.

In the group of surfactants c.8 preference is given to the ammonium salts and the alkaline metal salts of di($C_6$-$C_{12}$ alkyl) sulfosuccinates, $C_6$-$C_{12}$ alkyl being a straight chain or branched alkyl group of from 6 to 12 carbon atoms, e.g. n-hexyl, n-heptyl, n-octyl, n-nonyl, n-decyl, n-dodecyl, 2-hexyl, 2-heptyl, 2-octyl, 2-nonyl and 2-ethyl hexyl. Preferably, an alkaline metal dioctyl sulfosuccinate is employed, wherein the octyl moiety may be linear or branched and wherein the alkaline metal being selected from sodium and potassium. A particularly suitable example is Aerosol® OTB (Cytec), and the like.

In the group of surfactants c.9 the aryl sulfonic acid may be e.g. phenol sulfonic acid or naphthalene sulfonic acid which is unsubstituted or substituted by one or more, e.g. 1, 2, 3 or 4, $C_1$-$C_{20}$ alkyl groups. In a preferred embodiment, the surfactant c.9 is an alkaline metal salts or earth alkaline metal salt of a reaction product (condensate) of naphthalene sulfonic acid and formaldehyde; a particularly suitable example is Morwet® D425 (Akzo Nobel) In another preferred embodiment, the surfactant c.9 is an alkaline metal salt or earth alkaline metal salt of a reaction product (condensate) of phenol sulfonic acid, formaldehyde and urea; a particularly suitable example is Wettol® D1 (BASF SE).

Preferred graft or comb copolymers of the group c.12 preferably contain, in polymerised form, (i) at least one $C_3$-$C_5$ monoethylenically unsaturated carboxylic acid monomer, such as acrylic acid, methacrylic acid or maleic acid, (ii) at least one monomer having an oligo- or poly-$C_2$-$C_4$-alkylene oxide group, in particular an oligo- or polyethylenoxide group which is attached either via ester linkages or ether linkages to a polymerizable ethylenically unsaturated double bond, in particular an ester of an oligo- or poly-$C_2$-$C_4$-alkylene oxide, especially an ester of an oligo- or polyethylenoxide with a $C_3$-$C_5$ monoethylenically unsaturated carboxylic acid monomer, such as acrylic acid or methacrylic, or an ester of an oligo- or poly-$C_2$-$C_4$-alkylene oxide mono-$C_1$-$C_4$-alkylether, especially an ester of an oligo- or polyethylenoxide mono-$C_1$-$C_4$-alkylether with a $C_3$-$C_5$ monoethylenically unsaturated carboxylic acid monomer, such as acrylic acid or methacrylic, (iii) optionally hydrophobic monomers having a water solubility of not more than 60 g/l at 20° C. and 1013 mbar, e.g. $C_1$-$C_{10}$-alkylesters of $C_3$-$C_5$ monoethylenically unsaturated carboxylic acid monomers, in particular $C_1$-$C_{10}$-alkylesters of acrylic acid or methacrylic acid ($C_1$-$C_{10}$-alkylacrylates and $C_1$-$C_{10}$-alkylmethacrylates), e.g. methylacrylate, ethylacrylate, n-propylacrylate, isopropylacrylate, n-butylacrylate, isobutylacrylate, tert.-butylacrylate, methylmethacrylate, ethylmethacrylate, n-propylmethacrylate, isopropylmethacrylate, n-butylmethacrylate, isobutylmethacrylate, tert.-butylmethacrylate, vinylaromatic monomers such as styrene and $C_2$-$C_{12}$-monolefines such as ethene, propene, 1-butene, isobutene, hexene, 2-ethylhexene, diisobutene (mixture of isobuten dimers), tripropene, tetrapropene, triisobutene etc. In a preferred embodiment of the surfactants c.12, the graft or comb polymer contains or consists of, in polymerized form, methacrylic acid, methyl methacrylate and an ester of polyethylene oxide monomethylether with methacrylic acid, such as in the copolymer having CAS-No. 1000934-04-1 which is commercially available as Tersperse® 2500 or in the copolymer having CAS-No. 119724-54-8 which is commercially available as Atlox® 4913.

The weight-average molecular weight of the graft or comb copolymers of group c.12 is preferably in the range from 5000 to 800000 g/mol, in particular from 7500 to 600000 g/mol, especially from 10000 to 400000 g/mol. The graft or comb copolymers of group c.12 are preferably not crosslinked.

Preferred polymeric surfactants of the group c.13 are those which contain, in polymerized form (i) at least one $C_3$-$C_5$ monoethylenically unsaturated carboxylic acid monomer, and (ii) at least one hydrophobic monomer as defined above. Suitable $C_3$-$C_5$ monoethylenically unsaturated carboxylic acid monomer and suitable hydrophobic monomers are those mentioned in the group c.12. Preferred $C_3$-$C_5$ monoethylenically unsaturated carboxylic acid monomers include acrylic acid, methacrylic acid and maleic acid. Preferred hydrophobic monomers are selected from vinylaromatic monomers such as styrene monomers and $C_2$-$C_{12}$-monolefines. Preferably, the polymeric surfactants c.13 contain, in polymerised form, (i) at least one $C_3$-$C_5$ monoethylenically unsaturated carboxylic acid monomer, in particular acrylic acid or methacrylic acid, and (ii) at least one hydrophobic monomer selected from styrene monomers and $C_2$-$C_{12}$-monolefines. The weight ratio from acid monomer to hydrophobic monomer is preferably in the range of from 10:1 to 1:3; preferably from 5:1 to 1:2. A particularly suitable example for surfactants c.13 is Atlox® Metasperse 500L (Uniqema), and the like.

Non-ionic surfactants include in particular c.14 polyethyleneglycol-$C_1$-$C_{22}$-alkylethers, polyethyleneglycol/polypropyleneglycol-$C_1$-$C_{22}$-alkylethers, in particular polyethoxylates and poly-ethoxylates-co-propoxylates of linear or branched $C_8$-$C_{20}$-alkanoles, more preferably polyethoxylated $C_8$-$C_{22}$-fatty alcohols and polyethoxylated $C_8$-$C_{22}$-oxoalcohols, such as polyethoxylated lauryl alcohol, polyethoxylated isotridecanol, polyethoxylated cetyl alcohol, polyethoxylated stearyl alcohol, polyethoxylates-co-propoxylates of laurylalcohol, polyethoxylates-co-propoxylates of cetylalcohol, poly-ethoxylates-co-propoxylates of isotridecylalcohol, polyethoxylates-co-propoxylates of stearylalcohol, and esters thereof, such as acetates;

c.15 polyethylenglycol aryethers and polyethyleneglycol/polypropyleneglycol aryethers, in particular polyethoxylates and poly-ethoxylates-co-propoxylates of mono- or di-$C_1$-$C_{16}$-alkylphenoles, such as polyethoxylates and poly-ethoxylates-co-propoxylates of nonylphenol, decylphenol, isodecylphenol, dodecylphenol or isotridecylphenol, and esters thereof, such as acetates;

c.16 $C_6$-$C_{22}$-alkylglucosides and $C_6$-$C_{22}$-alkyl polyglucosides;

c.17 partial esters of polyols with $C_6$-$C_{22}$-alkanoic acids, in particular mono- and diesters of glycerine and mono-, di- and triesters of sorbitan, such as glycerine monostearate, sorbitanmonooleat, sorbitantristearat;

c.18 polyethoxylates of $C_6$-$C_{22}$-alkylglucosides and polyethoxylates of $C_6$-$C_{22}$-alkyl polyglucosides;

c.19 polyethoxylates and poly-ethoxylates-co-propoxylates of $C_6$-$C_{22}$-fatty amines;

c.20 polyethoxylates and poly-ethoxylates-co-propoxylates of $C_6$-$C_{22}$-fatty acids and polyethoxylates and polyethoxylates-co-propoxylates of hydroxyl $C_6$-$C_{22}$-fatty acids;

c.21 polyethoxylates of partial esters of polyols with $C_6$-$C_{22}$-alkanoic acids, in particular polyethoxylates of mono- and diesters of glycerine and polyethoxylates of mono-, di- and triesters of sorbitan, such as polyethoxylates of glycerine monostearate, polyethoxylates of sorbitanmonooleat, polyethoxylates of sorbitanmonostearat and polyethoxylates of sorbitantristearat;

c.22 polyethoxylates of vegetable oils or animal fats such as corn oil ethoxylate, castor oil ethoxylate, tallow oil ethoxylate;

c.23 polyethoxylates of fatty amines, fatty amides or of fatty acid diethanolamides.

c.24 polyethoxylates and poly-ethoxylates-co-propoxylates of mono-, di- and tristyrylphenols; and the esters thereof, e.g. the acetates; and c.25 non-ionic block copolymers comprising at least one poly(ethylene oxide) moiety PEO and at least one polyether moiety PAO derived from $C_3$-$C_{10}$-alkylene oxides and/or styrene oxide, in particular polyoxyethylene-polyoxypropylene-block copolymers.

c.26 non-ionic graft copolymers containing polyethylene oxide moiety PEO grafted on a non-ionic, hydrophilic polymeric backbone.

The terms polyethyleneglycol, polyethoxylates and polyethoxylated refer to polyether radicals derived from ethyleneoxide. Likewise, the term poly-ethoxylate-co-propoxylate refers to a polyether radical derived from a mixture of ethyleneoxide and propylenoxide. Thus polyethoxylates have repeating units of the formula [$CH_2CH_2O$] while polyethoxylate-co-propoxylate have repeating units of the formulae [$CH_2CH_2O$] and [$CH(CH_3)CH_2O$]. The surfactants c.14, c.15 and c.18 to c.24 may belong to the group of non-polymeric surfactants or to the group of polymeric surfactants, depending on the number of alkylene oxide repeating units. In the surfactants of these groups, the number of such repeating units will generally range from 2 to 200, in particular from 3 to 100, especially from 3 to 50. The surfactants of the groups c.17 and c.18 belong to non-polymeric surfactants while the surfactants of groups c.25 and c.26 are usually polymeric surfactants.

Amongst non-ionic surfactants those of the groups c.14, c.15, c.24, c.25 and c.26 and mixtures thereof are preferred.

In the group of surfactants c.14 preference is given to polyethoxylates and poly(ethoxylate-co-propoxylates) of linear $C_8$-$C_{22}$ alkanols. Likewise preferred are poly(ethoxylate-co-propoxylates) of $C_1$-$C_{10}$ alkanols, with particular preference given to butanol. Amongst the surfactants c.14 those are preferred which have a number average molecular weight $M_N$ of not more than 5000 Dalton.

In the group of surfactants c.15 preference is given to polyethoxylates and poly(ethoxylate-co-propoxylates) of mono- or $C_8$-$C_{22}$ alkanols. Likewise preferred are poly (ethoxylate-co-propoxylates) of $C_1$-$C_{10}$ alkanols, with particular preference given to butanol. Amongst the surfactants c.15 those are preferred which have a number average molecular weight $M_N$ of not more than 5000 Dalton. Particular preference is given to poly(ethoxylate-co-propoxylates) of $C_1$-$C_{10}$ alkanols, having a number average molecular weight $M_N$ of from 500 to 5000 Dalton Particularly suitable examples include Atlox® G 5000 (Akzo Nobel), Tergitol®XD and the like.

In the surfactants of the group c.24 a phenoxy radical carries 1, 2 or 3 styryl moieties and a polyethylene oxide moiety PEO or a poly(ethylenoxide-co-propylenoxide) moiety PEO/PPO. The PEO moiety typically comprises from 5 to 50 ethylene oxide groups. Preferred surfactants c.24 may be represented by the formula $(C_2H_4O)_n \cdot C_{30}H_{30}O$, wherein n is an integer of from 5 to 50 and $C_{30}H_{30}O$ represents a tri(styryl) phenol group. A particularly suitable example is Soprophor® BSU (Rhodia).

The non-ionic block copolymers of the surfactant class c.25 comprise at least one poly(ethylene oxide) moiety PEO and at least one hydrophobic polyether moiety PAO, which is generally derived from one or more $C_3$-$C_{10}$ alkylene oxides. The PAO moiety usually comprises at least 3, preferably at least 5, in particular 10 to 100 repeating units (number average) which are derived from one or more $C_3$-$C_{10}$ alkylene oxides, such as propylene oxide, 1,2-butylene oxide, cis- or trans-2,3-butylene oxide or isobutylene oxide, 1,2-pentene oxide, 1,2-hexene oxide, 1,2-decene oxide and styrene oxide, among which $C_3$-$C_4$ alkylene oxides are preferred. Preferably, the PAO moieties comprise at least 50% by weight, and more preferably at least 80% by weight of repeating units derived from propylene oxide. The PEO moieties usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 1:10 to 2:1, more preferably from 2:8 to 7:3 and in particular from 3:7 to 6:4. Those surfactants c25) are preferred which have a number average molecular weight $M_N$ ranging from more than 1200 to 100000 Dalton, preferably from 2000 to 60000 Dalton, more preferably from 2500 to 50000 Dalton and in particular from 3000 to 20000 Dalton. In general, the PEO moieties and the PAO moieties make up at least 80% by weight, and preferably at least 90% by weight, e.g. 90 to 99.5% by weight, of the non-ionic block copolymer surfactants c25). Suitable surfactants c25) are described e.g. in WO2006/002984, in particular those having the formulae P1 to P5 given therein.

The non-ionic block copolymer surfactants of the group c.25 described herein are commercially available e.g. under the trade names Pluronic®, such as Pluronic® P 65, P84, P 103, P 105, P 123, Pluronic PE 3500, PE 4300, PE 4400, PE 6200, PE 6400, PE 6800, PE 9200, PE 9400, PE 10300, PE 10400, PE 10500 and Pluronic® L 31, L 43, L 62, L 62 LF, L 64, L 81, L 92 and L 121 (BASF SE); Pluraflo® such as Pluraflo® L 860, L1030 and L 1060 (BASF SE); Tetronic®, such as Tetronic® 704, 709, 1104, 1304, 702, 1102, 1302, 701, 901, 1101, 1301 (BASF SE); Agrilan® AEC 167 and Agrilan® AEC 178 (Akcros Chemicals); Antarox® B/848 (Rhodia); Berol® 370 and Berol® 374 (Akzo Nobel Surface Chemistry); Dowfax® 50 C15, 63 N10, 63 N30, 64 N40 and 81 N10 (Dow Europe); Genapol® PF (Clariant); Monolan®, such as Monolan® PB, Monolan® PC, Monolan® PK (Akcros Chemicals); Panox® PE (Pan Asian Chemical Corporation); Symperonic®, such as Symperonic® PE/L, Symperonic® PE/F, Symperonic® PE/P, Symperonic® PE/T (ICI Surfactants); Tergitol® XD, Tergitol® XH and Tergitol® XJ (Union Carbide); Triton® CF-32 (Union Carbide); Teric PE Series (Huntsman); and Witconol®, such as Witconol® APEB, Witconol® NS 500 K (Akzo Nobel Surface Chemistry) and the like. Among these, the Pluronic® and the Pluraflo® block copolymers are preferred, particularly suitable examples being Pluronic® P105 and Pluraflo® 1060, and the like. Particular preference is also given to mono-$C_1$-$C_{10}$ alkylether of polyethylenoxid-polypropylenoxid-Block polmers having a number average molecular weight $M_N$ of from 1000 to 10000 Dalton. Particularly suitable examples include Atlox® G 5000 (Uniqema), Tergitol®XD and the like.

Preferred graft copolymers of the group c.26 contain, in polymerised form, (i) methyl esters or hydroxyl-$C_2$-$C_3$-alkyl esters of $C_3$-$C_5$ monoethylenically unsaturated carboxylic acid monomers, such as methyl acrylate, methyl methacrylate, hydroxyethyl acrylate and hydroxyethyl methacrylate and (ii) polyethylenoxide groups which are attached either via ester linkages or ether linkages to the polymer backbone. In a preferred embodiment, the backbone of the surfactants c.26 contains, in polymerized form, methyl methacrylate and polyethylene oxide esters of methacrylic acid.

In a preferred embodiment of the present invention, the emulsion comprises at least one polymeric surfactant having at least one polyether group, in particular a non-ionic polymeric surfactant having at least one polyether group, in particular at least one poly-$C_2$-$C_4$-alkylenether group, or an anionic polymeric surfactant having at least one polyether group, in particular at least one poly-$C_2$-$C_4$-alkyleneether group or mixtures thereof. Preferred polymeric surfactants having at least one polyether group, in particular at least one poly-$C_2$-$C_4$-alkyleneether group, are selected from the polymeric surfactant of the groups c.12, c.24 and c.25 and mixtures thereof.

In a preferred embodiment of the present invention, the emulsion comprises at least one non-ionic polymeric surfactant having at least one polyether group, in particular at least one poly-$C_2$-$C_4$-alkylenether group, in particular a non-ionic polymeric surfactant of the groups c.24 or c.25.

In a likewise preferred embodiment of the present invention, the emulsion comprises at least one anionic polymeric surfactant having polyether side chains, in particular an anionic polymeric surfactant which is a polymer having a carbons backbone carrying carboxylate groups and polyether side chains, especially an anionic polymeric surfactant of the group c.12, in particular a graft or comb polymer containing or consisting of, in polymerized form, methacrylic acid, methyl methacrylate and an ester of polyethylene oxide monomethylether with methacrylic acid, such as the copolymer having CAS-No. 1000934-04-1 which is commercially available as Tersperse® 2500 (Huntsman) or the copolymer having CAS-No. 119724-54-8 which is commercially available as Atlox® 4913 (Uniqema).

In a particular preferred embodiment of the present invention, the emulsion comprises at least one non-ionic polymeric surfactant having at least one polyether group, in particular a non-ionic polymeric surfactant of the groups c.24 or c.25 and at least one further surfactant, selected from non-polymeric non-ionic surfactants, anionic non-polymeric surfactants and anionic polymeric surfactants. Preferably the further surfactant is selected from the groups c.6, c.7, c.8, c.9, c.12, c.14 and c.15. In a particular preferred embodiment of the invention, the emulsion comprises at least one non-ionic polymeric surfactant, in particular a non-ionic polymeric surfactant of the groups c.24 or c.25 and at least one further surfactant, selected from anionic polymeric surfactants, in particular of the group c.12. In another particular preferred embodiment of the invention, the emulsion comprises at least one non-ionic polymeric surfactant, in particular a non-ionic polymeric surfactant of the groups c.24 or c.25 and at least one further surfactant, selected from anionic non-polymeric surfactants, in particular of the group c.6, c.7 or c.9.

The emulsion, which is provided in step a) of the process according to the present invention, can be prepared by any conventional processes for the preparation of aqueous emulsions of pesticide compounds.

Preferably, the emulsion is provided in a first step a1) at a temperature, where the organic pesticide compound remains in the form of molten droplets, i.e. in the form of droplets where the pesticide compound is present in the molten state.

The temperature, where the organic pesticide compound remains in the form of molten droplets, is generally above the melting point of the pesticide compound—the lowest melting point, if the pesticide compound is capable of existing as different polymorphs having different melting points—but may also be below its melting point, however preferably not less than 20 K, in particular not less than 10 K below the (lowest) melting point, in order to avoid uncontrolled solidification/crystallization. A temperature slightly below the melting point will generally be tolerated because crystallization will be slow in the absence of seeds and the molten pesticide compound may show a melting point depression, when emulsified in the presence of surfactants. Preferably the temperature of the emulsion, where the organic pesticide compound remains in the form of molten droplets, is in the range from −20 K to +50 K, in particular from −10 K to +40 K, relating to the (lowest) melting point of the pesticide compound. In case of pyraclostrobin the temperature, where the emulsified droplets of pyraclostobin remain in the molten state, will be generally in the range from 45 to 90° C., in particular from 50 to 80° C.

Then, in a second step a2), the emulsion is cooled to a temperature, which is significantly below the (lowest) melting point of the crystalline form of the pesticide compound. This temperature will generally be at least 5 K or at least 10 K below the (lowest) melting point of the pesticide compound, preferably at least 15 K below its (lowest) melting point in particular at least 20 K, e.g. from 10 to 60 K, preferably from 15 to 50 K, especially from 20 to 40 K below the (lowest) melting point of the pesticide compound. In case of pyraclostrobin the emulsion is preferably cooled to a temperature in the range from 5 to 50° C., preferably in the range from 10 to 45° C., in particular in the range from 15 to 40 or from 15 to 35° C.

Preferably, the emulsion of the pesticide compound is prepared by emulsifying the molten pesticide compound in water which may contain one or more surfactants. Preferably, the water contains one or more of the aforementioned surfactants in the aforementioned concentrations. As mentioned above, the temperature, where the molten pesticide compound is emulsified in water is chosen that the emulsified organic pesticide compound remains in the form molten droplets. Thus, the water may be preheated to the desired temperature or the melt is heated to a temperature that upon mixing the desired temperature is achieved. It is, of course, also possible to suspend the solid pesticide compound in water, which may contain may contain at least one or more surfactants and optionally further formulation additives, and heating the suspension to a temperature above the melting temperature of said pesticide compound.

When emulsifying the melt the pesticide droplets are usually comminuted to achieve the desired droplet size. The average droplet size, i.e. the volume average diameter of the droplets, is preferably in the range of from 0.5 to 10 µm, in particular in the range from 1 to 5 µm, as determined by dynamic light scattering.

Comminution is preferably achieved by applying shear during emulsification of the melt. Suitable devices for applying shear include any devices suitable for wet grinding (see e.g. H. Mollet et al "Formulation Technology" Wiley-VCH 2001, pp. 136-144). Examples include high shear mixers, such as Ultra-Turrax apparatus, and dissolvers, static mixers, e.g. systems having mixing nozzles, bead mills, vibratory mills, agitator bead mills, emulsifying centrifuges, colloid mills, cone mills, circulating mills (agitator ball mills with pin grinding system), disk mills, annular chamber mills, double cone mills, sprocket dispersers or homogenizers and other homogenizers. Shear may also be applied by turbulent mixing, injecting a fluid into another, oscillations and cavitation of the mixture (for example using ultrasound). The comminution is performed at a temperature, where the organic pesticide compound remains in the form of molten droplets.

Preferably is comminution is performed at a temperature in the range from −20 K to +50 K, in particular from −10 K to +40 K, relating to the (lowest) melting point of the pesticide compound. In case of pyraclostrobin comminution is performed at temperature in the range from 45 to 90° C., in particular from 50 to 80° C.

To the thus obtained aqueous emulsion, an aqueous suspension of the pesticide compound is added. Addition is preferably performed at a temperature of at least 5 K, frequently at least 10 K, preferably at least 15 K, in particular at least 20 K, below the (lowest) melting point of the pesticide compound, e.g. from 10 to 60 K, preferably from 15 to 50 K, especially from 20 to 40 K below the (lowest) melting point of the pesticide compound. In case of pyraclostrobin the addition is preferably performed at a temperature in the range from 5 to 50° C., preferably in the range from 10 to 45° C., in particular in the range from 15 to 40 or from 15 to 35° C.

The amount of suspension, which is added to the aqueous emulsion of the pesticide compound, is preferably chosen such that the amount of the organic pesticide compound contained in the aqueous suspension is from 0.01 to 0.3 parts by weight, in particular from 0.05 to 0.2 parts by weight, per 1 part by weight of the pesticide compound contained in the aqueous emulsion. Addition is preferably performed by mixing the aqueous emulsion with the aqueous suspension. Mixing will be generally performed by using a suitable mixing device. The type of mixing device is of minor importance, since crystallization occurs rapidly. Suitable mixing devices include standard vessels containing one or more stirrers. It is also possible to perform addition/mixing in one of the aforementioned comminution devices which have been mentioned in connection with emulsification. It may be favourable, though not necessary, to continue comminution after addition of the aqueous suspension to the emulsion until the desired particle size is achieved. However, in the process of the present invention, crystallization rate will generally be very rapid and generally completed within seconds or minutes. Thus further comminution after addition of the aqueous suspension to the emulsion is generally not required.

In the aqueous suspension, which is added to the aqueous emulsion of the pesticide compound, the pesticide compound is present in essentially crystalline form. In a preferred embodiment of the invention, the pesticide compound contained in the aqueous emulsion is pyraclostrobin and the pesticide contained in the aqueous suspension is a crystalline polymorph of pyraclostrobin, in particular a crystalline form which is essentially, i.e. at least 90% by weight, based on the amount of pyraclostrobin present in the suspension, modification IV as described above or in WO 2006/136357.

The concentration of the organic pesticide compound in the aqueous suspension that is added to the emulsion is generally from 1 to 60% by weight, in particular from 5 to 50% by weight, especially from 10 to 40% by weight.

It has been found to be favourable, when the volume average particle size of the crystalline pesticide compound present in the aqueous suspension which is added to the emulsion in step b), i.e. the volume average diameter of the crystalline pesticide compound particles in the aqueous suspension that is added to the emulsion, is from 0.2 to 10 µm, in particular from 0.5 to 8 µm and especially from 1 to 5 µm.

The aqueous suspension, which is added to the aqueous emulsion of the pesticide compound, may contain one or more surfactants and may further contain further formulation additives. The surfactants, which are contained in the aqueous suspension, may be identical with or different from the surfactants contained in the aqueous emulsion. Preferably, the surfactants that are contained in the suspensions are similar to those which are contained in the emulsions. Preferred surfactants and surfactant combinations are those, which are mentioned as preferred surfactant and surfactant combinations in connection with the aqueous emulsions. The concentration of surfactant in the aqueous suspension is generally in the range from 0.1 to 20% by weight, preferably from 0.5 to 15% by weight and in particular from 1 to 10% by weight, based on the total weight of the aqueous suspension. Usually, the weight ratio of the pesticide to the surfactant is in the range of from 2:1 to 50:1, and particularly from 3:1 to 20:1.

The crystalline pesticide compound contained aqueous suspension, which is added to the aqueous emulsion of the pesticide compound, is of course the same as the pesticide compound contained in the aqueous emulsion. However, the aqueous suspension may additionally contain one or more further pesticide compounds. These further pesticide compounds may be water soluble or of limited water-solubility as described below Preferably, the crystalline pesticide compound contained in the suspension, which is the same as the pesticide compound contained in the emulsion, amounts to at least 20% by weight, in particular at least 40% by weight, of the total amount of pesticide compound contained in the suspension.

In a preferred embodiment of the invention, the pesticide compound contained in the aqueous emulsion is pyraclostrobin and the pesticide contained in the aqueous suspension which is added to the emulsion is a crystalline polymorph of pyraclostrobin, in particular a crystalline form which is essentially, i.e. at least 90% by weight, based on the amount of pyraclostrobin present in the suspension, modification IV as described above or in WO 2006/136357.

The aqueous suspension to be added to the aqueous emulsion of the pesticide compound can be prepared by standard procedures for the preparation of aqueous suspensions of organic pesticide compounds. Generally, the aqueous suspension will be prepared by suspending the solid pesticide compound, which is essentially crystalline, in water which may contain one or more surfactants to stabilize the pesticide compound particles followed by comminution of the suspended pesticide compound to the desired particle size. Comminution can be performed similar to the procedure described for comminution of the emulsion droplets.

It is a particular benefit of the process according to the present invention that a separate preparation of the aqueous suspension to be added to the aqueous emulsion is required only in an initial phase of the process. Once, the aqueous suspension has been added to the aqueous emulsion of the pesticide compound, an aqueous suspension of the pesticide compound is formed, wherein the pesticide compound particles are essentially crystalline. The particle size of the pesticide compound particles will generally in the range given for the aqueous emulsion. Therefore, the thus obtained suspension (or a portion thereof) can be used as the suspension to be added to the aqueous emulsion during a further run of the inventive process. It is thus possible to perform the process of the present invention as a simple batch process but also as a semi-continuous process or a continuous process simply by taking a portion of the aqueous suspension formed when the aqueous suspension is added to the aqueous emulsion and recycling this portion into step b) of the claimed process. This portion will generally be from 0.01 to 0.3 parts by weight, in particular from 0.05 to 0.2 parts by weight, per 1 part by weight of the aqueous suspension formed in step b). Thereby the process of the present invention almost completely avoids the tedious preparation and handling of solid crystalline pesticide compound material.

As stated above, step b) of the process of the present invention yields an aqueous suspension of the pesticide compound, wherein the pesticide compound particles are essentially crystalline. The particle size of the pesticide compound particles, i.e. the volume average diameter of the crystalline pesticide compound particles, is generally in the range of from 0.5 to 10 μm, in particular in the range from 0.8 to 8 μm and especially in the range from 1 to 5 μm, as determined by dynamic light scattering.

The concentration of the organic pesticide compound in the aqueous suspension which is obtained in step b) is generally from 1 to 60% by weight, in particular from 5 to 50% by weight, especially from 10 to 40% by weight, based on the total weight of the aqueous suspension.

The aqueous suspension obtained in step b) will generally contain the one or more surfactants contained in the aqueous emulsion and in the aqueous suspension of the pesticide compound that has been added to the aqueous emulsion. In general, the aqueous suspensions obtained in step b) of the process contain at least one surfactant in amounts from 0.1 to 20% by weight, preferably from 0.5 to 15% by weight and in particular from 1 to 10% by weight, based on the total weight of the suspension. Usually, the weight ratio of the pesticide to the surfactant is in the range of from 2:1 to 50:1, and particularly from 3:1 to 20:1. It has been found to be advantageous for the stability of the obtained suspension that the surfactant(s) is (are) chosen from those surfactant and surfactant combinations which have been mentioned as preferred or particular preferred surfactants in connection with the surfactants contained in the aqueous emulsion of the pesticide compound.

As stated above, the aqueous suspension which is obtained in step b) of the process according to the present invention may be used as such as an aqueous suspension concentrate formulation of the pesticide compound. The aqueous suspension which is obtained in step b) of the process according to the present invention may, however, also be used as a base for preparing a stable formulation, in particular an aqueous suspension concentrate, which contains said organic pesticide compound, optionally together with one or more further formulation additives and/or with one or more further organic or inorganic pesticide compounds.

The term "aqueous suspension concentrate", as used herein, includes any pesticide formulation, wherein the pesticide compound is present in the form of particles which are suspended in an aqueous phase. The aqueous phase my be water or a mixture of water containing up to 20% by volume, based on the total volume of the aqueous phase, of a water miscible solvent, e.g. the anti-freeze agent as described herein. The aqueous phase may also contain, dissolved therein, one or more surfactants and/or one or more dissolved water-soluble pesticide compounds which do not count in the aqueous phase. In particular, the term "aqueous suspension concentrate", as used herein, includes aqueous suspension concentrates for field application, which are also termed as SC formulations, as well as aqueous suspension concentrate formulations for seed treatment, which are also referred to as FS formulations.

The one or more further formulation additives may be simply added to the aqueous suspension obtained in step b), preferably using a mixing device such as a stirrer or static mixer in order to achieve homogenous distribution of the formulation additive in the final formulation. The formulation additive may be added as such or in the form of an aqueous suspension or solution.

Principally any customary formulation additive can be added. The customary formulation additives might depend on the active ingredient in a known manner and include, for example, anti-freeze agents, viscosity-modifying agents (thickeners or rheology modifying agents), antifoams (also termed defoamers or defoaming agenss), bactericides, coloring agents such as dyes or pigments, and binders. Such additives may be incorporated into the aqueous suspension concentrate either before or after step b) of the preparation process described herein has been carried out. Preferably, the majority or all of these additives are added after step b) of the preparation process described herein has been carried out. The amount of additives, different from antifreeze agents, will generally not exceed 10% by weight, in particular 5% by weight of the total weight of the composition.

Suitable antifreeze agents include mono- and polyols, in particular $C_1$-$C_4$ alkanols and polyhydric $C_2$-$C_4$ alcohols. Examples for $C_1$-$C_4$ alkanols include e.g. methanol, ethanol, n-propanol and isopropanol. Examples for polyhydric $C_2$-$C_4$ alcohols include ethylene glycol, 1,2-propane diol, 1,3-propane diol, glycerol and 1,4-butane diol. Preferred anti-freeze agents are selected from the group of polyhydric $C_2$-$C_4$ alcohols and more preferably from ethylene glycol and 1,3-propane diol. The concentration of antifreeze agents in the final suspension concentrates will generally not exceed 20% by weight, based on the total weight of the final suspension concentrate, and is preferably in the range from 0.1 to 20% by weight, in particular from 0.5 to 10% by weight and especially from 1 to 5% by weight, based on the total weight of the final suspension concentrate.

Suitable thickeners are compounds which affect the flow behavior of the suspension concentrate and may assist in stabilizing the suspension concentrate against caking. Mention may be made, in this connection, for example, of commercial thickeners based on polysaccharides, such as methylcellulose, carboxymethylcellulose, hydroxypropylcellulose (Klucel® grades), Xanthan Gum (commercially available e.g. as Kelzan® grades from Kelco or Rhodopol® grades from Rhodia), synthetic polymers such as acrylic acid polymers (Carbopol® grades), polyvinyl alcohol (e.g. Mowiol® and Poval® grades from Kuraray) or polyvinyl pyrrolidones, silicic acid or phyllosilicates such as montmorillonites, attapulgites and bentonites, which may be hydrophobized, (commercially available as Attaclay® grades and Attaflow® grades from BASF SE; or as Veegum® grades and Van Gel® grades from R.T. Vanderbilt). Xanthan Gum and phyllosilicates, and especially mixtures thereof are preferred thickeners. The concentration of thickeners in the final suspension concentrates will generally not exceed 2% by weight, based on the total weight of the final suspension concentrate, and is preferably in the range from 0.01 to 2% by weight, in particular from 0.02 to 1.5% by weight and especially from 0.1 to 1% by weight, based on the total weight of the final suspension concentrate.

Antifoam agents may be added to the suspension concentrates. Examples of suitable antifoam agents include e.g. silicone emulsions (such as, for example, Drewplus® grades Silikon® SRE, Wacker or Rhodorsil® from Rhodia), long-chain alcohols, fatty acids, organofluorine compounds and mixtures thereof.

Bactericides can be added to stabilize the suspension concentrates against attack by microorganisms. Suitable bactericides are, for example, based on isothiazolones such as the compounds marketed under the trademarks Mergal® K10, Proxel® grades from Avecia (or Arch) or Acticide® grades such as Acticide® MBS or Acticide® RS from Thor Chemie and Kathon® grades such as Kathon® MK from Rohm & Haas.

The compositions of the invention may optionally comprise also coloring agents such as pigments or dyes, in particular, if the composition is intended for seed treatment purposes. Suitable pigments or dyes for seed treatment formulations are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

In addition, the aqueous suspensions obtained by the process according to the invention can be formulated with conventional binders, for example aqueous polymer dispersions, water-soluble resins, for example water-soluble alkyd resins, or waxes, in particular, if the composition is intended for seed treatment purposes.

Furthermore, the aqueous suspensions obtained by the process according to the invention can be formulated with further pesticide compounds. The nature of the further pesticide compound will naturally depend on the pesticide compound contained in the aqueous suspension obtained in step b). Likewise, the concentration of the further pesticide compound and the weight ratio of the first pesticide compound which contained in the aqueous suspension obtained in step b) and the further pesticide compound will depend in a known manner from the type of first and second pesticide compound.

The pesticide compound can be any organic or inorganic pesticide compound, which is suitable as a co-pesticide for the pesticide compound which is contained in the aqueous suspension obtained in step b). The further pesticide compound may be water soluble or may have limited water solubility as defined herein, the latter being preferred.

The further pesticide compound may be added as a solid material, e.g. as a powder. In this case, the obtained mixture will be generally subjected to a further comminution step of the thus obtained mixture. Comminution is preferably achieved by applying shear to the mixture of the aqueous suspension and the further pesticide compound. Suitable devices for applying shear include any high shear devices mentioned above, e.g. high shear mixers, such as Ultra-Turrax apparatus, and dissolvers, static mixers, e.g. systems having mixing nozzles, bead mills, vibratory mills, agitator bead mills, colloid mills, cone mills, circulating mills (agitator ball mills with pin grinding system), disk mills, annular chamber mills, double cone mills, sprocket dispersers or homogenizers and other homogenizers. The comminution is performed at a temperature, where the first and any further organic pesticide compound remain in the form of solid particles. Preferably is comminution is performed at a temperature of at least 10 K below the (lowest) melting point of any pesticide compound present.

The further pesticide compound may also be added as a liquid, e.g. as an aqueous solution or suspension. In this case, it will not be necessary but possible to subject the obtained mixture to a further comminution step. Generally, the addition of the liquid which contains the at least one further pesticide compound performed by using a mixing device such as a stirrer or static mixer in order to achieve homogenous distribution of the liquid composition contain the at least one further pesticide compound in the final formulation. The liquid containing the further pesticide compound may contain one or more surfactants and/or formulation additives.

Further formulation additives may also be added during or after the addition of the further pesticide compound.

The total concentration of any organic pesticide compound in the aqueous suspension concentrate formulation is generally from 1 to 60% by weight, in particular from 5 to 55% by weight, especially from 10 to 50% by weight, based on the total weight of the aqueous suspension. The relative amount of the first (crystalline) pesticide compound and the at least one further pesticide compound is generally from 20:1 to 1:20 and in particular from 10:1 to 1:10 (weight ratio).

The thus obtained formulation have the form of an aqueous suspension (i.e. in the form of an aqueous suspension concentrate), which contains the first pesticide compound in the form of suspended particles which are essentially crystalline and at least one further pesticide compound, which may be present in the form of solid particles or in dissolved form, depending on the solubility of the at least one further pesticide compound in water. The particle size of the pesticide compound particles, i.e. the volume average diameter of any solid compound particles, is generally in the range of from 0.5 to 10 µm, in particular in the range from 0.8 to 8 µm and especially in the range from 1 to 5 µm, as determined by dynamic light scattering.

As mentioned above, the further pesticide compound may be selected from any pesticide compound which is known to be suitable for co-formulation with the first pesticide compound. The further pesticide compound will be generally selected from organic pesticide compounds, in particular from the group of organic fungicide compounds, organic insecticide compounds and organic herbicide compounds.

Suitable further pesticides for the purpose of the invention include but are not limited to: organic fungicides, in particular azole fungicides such as metconazol, epoxiconazol, triticonazol, fluquinconazol, prothioconazol, difenoconazol or cyproconazol;

amide fungicides such as carboxin, oxycarboxin, cyazofamid, boscalid, isopyrazam, bixafen, penflufen, penthiopyrad, sedaxane, isothianil, N-(3',4',5'-trifluorobiphenyl-2-yl)-1-methyl-3-difluoromethyl-1H-pyrazole-4-carboxamid (common name: fluxapyroxad), N-(4'-trifluoromethylthiobiphenyl-2-yl)-1-methyl-3-difluoromethyl-1H-pyrazole-4-carboxamid or other fungicides such as dithianon, pyrimethanil, metiram, mancozeb, captan, folpet, chlorothalonil or thiophanat-methyl, insecticides in particular phenylpyrazole insecticides such as fipronil or chlorantraniliprole, pyretroid insecticides such as α-cypermethtrin, neonicotinoids such as clothianidin, thiamethoxam or imidacloprid, further insecticides such as abamectin, teflubenzuron or metaflumizone, herbicides such as glyphosate, glufosinate, imazomox, imazapyr, imazapic, imazethapyr or dicamba, and growth inhibitors or growth retardants such as mepiquat or chlormequat;

and, where possible, the salts of the aforementioned compounds.

If pyraclostrobin is the first pesticide compound, suitable pesticide compounds which may be co-formulated with pyraclostrobin include e.g.

organic fungicides, in particular azole fungicides such as metconazol, epoxiconazol, triticonazol, fluquinconazol, prothioconazol, difenoconazol or cyproconazol;

amide fungicides such as carboxin, oxycarboxin, cyazofamid, boscalid, isopyrazam, bixafen, penflufen, penthiopyrad, sedaxane, isothianil, N-(3',4',5'-trifluorobiphenyl-2-yl)-1-methyl-3-difluoromethyl-1H-pyrazole-4-carboxamid, N-(4'-trifluoromethylthiobiphenyl-2-yl)-1-methyl-3-difluoromethyl-1H-pyrazole-4-carboxamid or other fungicides such as dithianon, pyrimethanil, metiram, mancozeb, captan, folpet, chlorothalonil or thiophanat-methyl, insecticides in particular phenylpyrazole insecticides such as fipronil or chlorantraniliprole, pyretroid insecticides such as α-cypermethrin, neonicotinoids such as clothianidin, thiamethoxam or imidacloprid, further insecticides such as abamectin, teflubenzuron or metaflumizone, herbicides such as glyphosate, glufosinate, imazomox, imazapyr, imazapic, imazethapyr or dicamba, and growth inhibitors or growth retardants such as mepiquat or chlormequat;

and, where possible, the salts of the aforementioned compounds.

In preferred embodiments of the invention, the first pesticide compound is pyraclostrobin and the further pesticide compound is selected from the group of amide fungicides as mentioned above, in particular from the group consisting of penflufen, sedaxane, penthiopyrad, fluxapyroxad and N-(4'-trifluoromethylthiobiphenyl-2-yl)-1-methyl-3-difluoromethyl-1H-pyrazole-4-carboxamid.

In another preferred embodiments of the invention, the first pesticide compound is pyraclostrobin and the further pesticide compound is selected from the group of conazole fungicides as mentioned above, in particular from the group consisting of methconazol, epoxiconazol and mixtures of epoxiconazol with fipronil.

In a particular embodiment of the invention, the first pesticide compound is pyraclostrobin and the further pesticide compound is metconazol. In another particular embodiment of the invention, the first pesticide compound is pyraclostrobin and the further pesticide compound is epoxiconazol. In yet a further particular embodiment of the invention, the first pesticide compound is pyraclostrobin and the further pesticide compound is boscalid. In yet a further particular embodiment of the invention, the first pesticide compound is pyraclostrobin and the further pesticide compound is fluxapyroxad. In yet a further particular embodiment of the invention, the first pesticide compound is pyraclostrobin and the further pesticide compound is a mixture of fipronail and epoxiconazol. In yet a further particular embodiment of the invention, the first pesticide compound is pyraclostrobin and the further pesticide compound is dithianon. In yet a further particular embodiment of the invention, the first pesticide compound is pyraclostrobin and the further pesticide compound is chlorothalonil.

The aqueous suspension concentrates obtained by the process according to the invention are physically and chemically stable formulations, which can be stored over weeks or month or even years at ambient or elevated temperatures or varying temperatures without formation of noticeable amounts of coarse material or caking. The suspension concentrates are dilution stable, even after prolonged storage, i.e. upon dilution with water they do not show noticeable separation of active ingredient or creaming. Without being bound to a theory it is believed that the stability of the aqueous suspension concentrates obtained by the process according to the invention can be ascribed to a more regular form of the crystalline pesticide compound particles in contrast to the pesticide compound particles in aqueous suspension concentrates obtained by standard procedures including the comminution of crystalline material.

The aqueous suspension concentrates obtained by the process according to the invention can be obtained in any fields in which other formulations of the respective pesticide compounds are used. For example, if the pesticide compound contained in the aqueous suspension concentrate is pyraclostrobin, the suspension concentrate can be used for combating a multitude of harmful fungi on various cultivated plants, such as wheat, rye, barley, triticale, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants. It is of course possible to use the aqueous suspension concentrates obtained by the process according to the invention as a tank-mix partner with other formulations. For example, if the pesticide compound contained in the aqueous suspension concentrate is pyraclostrobin, the suspension concentrate can be applied with a large number of different pesticide compound formulations mentioned in WO 2006/136357 or with one or more of the further pesticides mentioned above.

The following examples will further illustrate the present invention.

Materials

Surfactant 1: poly(ethylene glycol block propylene glycol) butylether having a HLB value of 17 (Atlox® G5000 of Uniqema).

Surfactant 2: sodium salt of a naphthalene formaldehyde condensate (Morwet® D425, Akzo Nobel)

Surfactant 3: comb polymer of methyl methacrylate, methacrylic acid and (methoxypolyethylene glycol)methacrylate, 33% solution in 1:1 mixture propylene glycol/water (commercially available, for example as Atlox® 4913 from Uniqema).

Surfactant 4: poly(ethylene glycol block propylene glycol block polyethylene glycol) (Pluronic PE 10500)

Surfactant 5: sodium salt of a phenolsulfonic urea formaldehyde condensate (Wettol D1, BASF SE)

Surfactant 6: Ammonium salt of the semisulfate of an ethoxilated tristyrylphenol (Soprophor 4D384)

Thickener 1: Xanthan Gum, Kelzan® S (Kelco).

Thickener 2: Liquid Attapulgite suspension (21% b.w.: Attaflow® FL of BASF SE).

Thickener 3: 1% b.w. aqueous solution of Xanthan Gum (Rhodopol® 23) in water containing 2% b.w. of propylene glycol and 0.5% b.w. of bactericide Defoamer: Drewplus® L768 (Ashland)

Analytics:

Particle size of the aqueous emulsions and suspensions were determined on appropriate dilutions by laser light scattering using a Malvern Mastersizer 2000. The particle size distributions are calculated by a interpretation of the sample's scattering pattern using the Fraunhofer model.

X-ray powder diffractograms were taken after deformulation of the active ingredient from the suspension using a D-5000 diffractometer from Siemens in reflection geometry in the range from $2\theta=4°-35°$ with increments of $0.02°$ using Cu—Kα radiation at 25° C. The 2θ values found were used to calculate the stated interplanar spacing d.

Melting points and heats of fusion were determined by DSC using a Simultaneous Thermal Analyzer STA 449 C Jupiter from NETZSCH with a heating rate of 5 K/min in the range from −5° to +80° C. The amount of sample was 5 to 10 mg. Integrating the melting peak provides both the heat of fusion of the sample (joules/gram), and the inflection point in which the sample begins to melt, called the onset of melt.

A conventional polarizing microscope equipped with a hot stage was used to observe crystallinity of the pesticide compound material.

The active ingredients are determined by reverse-phase HPLC using an L-Column ODS® column (150×4.6 mm, df=5 micron) with internal standard calibration and peak area ratio. An injection volume of about 2 μL is separated using a wavelength of about 280 nm at a column temperature of 55°

C. The mobile phase is a gradient consisting of acetonitrile, methyl-t-butyl ether, water, isopropyl alcohol, methanol, and phosphoric acid.

Syneresis:

On aging, a suspension concentrate may phase separate creating a transparent layer of continuous phase on top, supported by a milky layer of dispersed phase. This process is called syneresis: an expulsion of the liquid continuous phase in a suspension concentrate on storage. The separate material (%) is a measure of the syneresis (%). This is the volume of syneresis liquid (clear liquid on top) divided by the total sample volume expressed as a percentage. Samples with syneresis values of 10% or less are considered acceptable. Samples with syneresis values of less than 1% showed minimal separation, and are considered excellent.

Preliminary Test for Crystallization-Inhibiting Active Ingredient Mixture

A conventional suspension concentrate of pyraclostrobin (see e.g. reference example 1 described below) was melted on a microscope slide at a temperature of 70° C., and allowed to return to 25° C. This created a film of solid amorphous pyraclostrobin. Seed crystals of modification I and modification IV were sprinkled on the amorphous layer and the crystals were observed in 15 minute intervals. It could be seen that the crystals grew for a period of more than 4 h the growing crystals having the shape of the initial seed crystals. This demonstrates that the final crystal structure (for pyraclostrobin) is established by the seed crystal type.

Preparation Procedure

Preparation of Suspension Concentrates According to Standard Wet Grinding Processes (Reference Examples)

Reference Example 1

Into 55 grams of water, 3 grams of surfactant 2 and 2 grams of surfactant 1 were dissolved and then mixed until homogeneous. Then 40 grams of crystalline pyraclostrobin were added and dispersed using a high shear mixer. The 40% slurry was passed through Eiger Mini 50 bead mill using 0.8 mm beads with a 90% bead loading until a particle size of about 2.0 µm was achieved.

Reference Example 2

Into 40 kg of water, 10 kg of propylene glycol, and 5 kg surfactant 2 were dissolved and then mixed until homogeneous. Then 45 kg of crystalline pyraclostrobin were added and dispersed using a high shear mixer. The 45% slurry was passed through Drais 5 liter bead mill using 1.0 mm beads with a 70% bead loading until a particle size of 2.0 µm was achieved.

Reference Example 3

Into 55 grams of water, 7 grams of ethylene glycol, 5 grams of surfactant 2 and 3 grams of surfactant 4 were dissolved and then mixed until homogeneous. Then 30 grams of crystalline pyraclostrobin were added and dispersed using a high shear mixer. The 30% slurry was passed through Dynomill bead mill using 0.8 mm beads with a 80% bead loading until a particle size of 2.0 µm was achieved.

Reference Example 4

Into 16.4 grams of water, 1.1 grams of surfactant 3 and 1.1 grams of surfactant 1 were dissolved then mixed until homogeneous. Then 10.0 grams of crystalline pyraclostrobin of modification IV were added and the slurry was milled in an Eiger media mill using 80% loading of 1 mm glass beads until a final particle size of 1 µm was achieved. This produces an aqueous suspension where pyraclostrobin is present as its crystalline modification IV.

The process was repeated on a larger scale and the thus obtained suspension was diluted to a 21-25% by weight active ingredient concentration with further formulation additives added to yield the final suspension concentrate shown in table 2.

Reference Example 5

Into 16.4 grams of water, 1.1 grams of surfactant 2 and 1.1 grams of surfactant 1 were dissolved then mixed until homogeneous. Then 10.0 grams of crystalline pyraclostrobin of modification IV were added and the slurry was milled in an Eiger media mill using 80% loading of 1 mm glass beads until a final particle size of 1 µm was achieved. This produces an aqueous suspension where pyraclostrobin is present as its crystalline modification IV.

The process was repeated on a larger scale and the thus obtained suspension was diluted to an 21-25% by weight active ingredient concentration with further formulation additives added to yield the final suspension concentrate shown in table 2.

Preparation of Suspension Concentrates According to the Processes of the Invention Example 1

Into 97.9 grams of water, 6.3 grams of surfactant 1 and 6.3 grams of surfactant 3 were dissolved then mixed until homogeneous. Then 60.6 grams of molten pyraclostrobin were added and the mixture was pumped through a colloid mill, until a pyraclostrobin emulsion of about 3 µm had been formed. Microscopy of the emulsion direct after formation and after 24 h revealed that the pyraclostrobin contained in the emulsion was completely amorphous and remained amorphous for at least 24 h.

To this emulsion, 28.6 grams of aqueous suspension of reference example 4 were added and mixed in a glass container. After 15 seconds, a microscopic sample indicated complete crystallization. Determination of heat of fusion by DSC measurement implied that the crystalline material was modification IV of pyraclostrobin. P-XRD of the deformulated pyraclostrobin confirmed that the crystalline material was essentially modification IV of pyraclostrobin.

Example 2

Into 97.9 grams of water, 6.3 grams of surfactant 1 and 6.3 grams of surfactant 3 were dissolved then mixed until homogeneous. Then 60.6 grams of molten pyraclostrobin were added and the mixture was pumped through a colloid mill, until a pyraclostrobin emulsion of about 3 microns had been formed. Microscopy of the emulsion direct after formation and after 24 h revealed that the pyraclostrobin contained in the emulsion was completely amorphous and remained amorphous for at least 24 h.

To this emulsion, 28.6 grams of aqueous suspension of reference example 4 were added and the mixture was allowed to continue through the colloid mill. After 15 seconds, a microscopic sample indicated complete crystallization. Determination of heat of fusion by DSC measurement implied that the crystalline material was modification IV of pyraclostrobin. P-XRD of the deformulated pyraclostrobin confirmed that the crystalline material was essentially modification IV of pyraclostrobin. The thus obtained suspension was diluted to a 21-25% by weight active ingredient concentration with further formulation additives added to yield the final suspension concentrate shown in table 2.

Example 3

Example 3 was performed by the method described for example 2 with the following amendments. The suspension of reference example 5 was used instead of the suspension of reference example 4 and surfactant 3 was replaced by the same amount of surfactant 2. The thus obtained suspension was diluted to a 21-25% by weight active ingredient concentration with further formulation additives added to yield the final suspension concentrate shown in table 2.

TABLE 2

| Mill Base | Ref. Example 4 | Example 2 | Ref. Example 5 | Example 3 |
|---|---|---|---|---|
| Pyraclostrobin | 21.0% | 25.0% | 21.0% | 23.0% |
| Surfactant 1 | 3.8% | 3.8% | 3.8% | 3.8% |
| Surfactant 2 | 0.0% | 0.0% | 3.8% | 3.8% |
| Surfactant 3 | 3.8% | 3.8% | 0.0% | 0.0% |
| Propylene glycol | 2.5% | 2.5% | 2.5% | 2.5% |
| Thickener 1 | 0.2% | 0.2% | 0.2% | 0.2% |
| Thickener 2 | 0.4% | 0.4% | 0.4% | 0.4% |
| Defoamer | 0.1% | 0.1% | 0.1% | 0.1% |
| Water | to 100% | to 100% | to 100% | to 100% | all amounts are given in % by weight.

The formulations were stored for 4 weeks at 40° C. and 50° C., respectively. After that time the formulations were analysed with regard to heat of fusion, onset of melting, active ingredient content and particle size and compared with the initial value. The results are presented in the following tables 3 to 6:

TABLE 3

Formulation according to reference example 4

|  | initial | 4 weeks @ 40° C. | 4 weeks 50° C. |
|---|---|---|---|
| AI content [%][1] | 21.0 | 21.0 | 21.0 |
| Onset of melt [° C.] | 53.0 | 54.0 | 54.8 |
| Heat of Fusion [J/g] | 76.7 | 76.7 | 76.2 |
| Syneresis [%] | 0 | ~0.01 | ~0.01 |
| $D_{50}$ [µm] | 1.70 | 2.10 | 2.89 |

[1])Concentration of active ingredient in % by weight

TABLE 4

Formulation according to example 2

|  | initial | 4 weeks @ 40° C. | 4 weeks 50° C. |
|---|---|---|---|
| AI content [%][1] | 25.1 | 25.2 | 25.2 |
| Onset of melt [° C.] | 52.8 | 52.8 | 53.0 |
| Heat of Fusion [J/g] | 76.1 | 75.3 | 75.9 |
| Syneresis [%] | 0 | 0.01 | ~0.01 |
| $D_{50}$ [µm] | 2.61 | 2.50 | 2.73 |

TABLE 5

Formulation according to reference example 5

|  | initial | 4 weeks @ 40° C. | 4 weeks 50° C. |
|---|---|---|---|
| AI content [%][1] | 20.9 | 20.7 | 21.0 |
| Onset of melt [° C.] | 52.0 | 52.4 | 54.9 |
| Heat of Fusion [J/g] | 75.3 | 75.9 | 77.0 |
| Syneresis [%] | 0 | 10 | 10 |
| $D_{50}$ [µm] | 1.41 | 1.75 | 2.54 |

TABLE 6

Formulation according to example 3

|  | initial | 4 weeks @ 40° C. | 4 weeks @ 50° C. |
|---|---|---|---|
| AI content [%][1] | 23.2 | 23.0 | 23.2 |
| Onset of melt [° C.] | 51.1 | 51.9 | 54.8 |
| Heat of Fusion [J/g] | 71.0 | 71.4 | 71.0 |
| Syneresis [%] | 0 | 10 | 10 |
| $D_{50}$ [µm] | 1.66 | 2.19 | 2.64 |

The results summarized in tables 3 to 6 show that the formulations obtained by the process of the present invention are of similar stability as suspensions concentrates prepared by conventional processes.

Example 4

Preparation of an Aqueous Suspension Concentrate Containing Pyraclostrobin and Metconazol (a) Into 21.2 grams of water, 2.2 grams of surfactant 3 and 2.2 grams of surfactant 1 were dissolved then mixed until homogeneous. Then 13.8 grams of crystalline pyraclostrobin of modification IV was added and the slurry was milled in a bead mill using 80% loading of 1 mm glass beads until a final particle size of 1.5 µm was achieved (volume average diameter). The suspension was filtered using a 100 mesh sieve to remove unmilled material and chipped beads. This produces a 35% b.w. aqueous suspension where pyraclostrobin is present as its crystalline modification IV.

(b) Into 191 grams of water, 19.6 grams of surfactant 3 and 19.6 grams of surfactant 1 were dissolved then mixed until homogeneous. 0.4 g of defoamer were added and the mixture was heated to 65-75° C. To this solution 124 g of molten pyraclostrobin (70 to 85° C.) were added and the mixture was pumped through a colloid mill, until a pyraclostrobin emulsion of less than 10 microns had been formed. The emulsion was cooled to 35-40° C. while continuing to pass the mixture through the colloid mill. To this emulsion, 39.4 grams of the aqueous suspension of step (a) was added at 23 to 40° C. and the mixture was allowed to continue through the colloid mill for 15 min. The thus obtained suspension was filtered using a 100 mesh sieve to remove large material.

A microscopic sample of the suspension indicated complete crystallization. Determination of heat of fusion by DSC measurement implied that the crystalline material was modification IV of pyraclostrobin. P-XRD of the deformulated pyraclostrobin confirmed that the crystalline material was essentially modification IV of pyraclostrobin. The thus obtained suspension contained 35% by weight of pyraclostrobin and the volume average diameter of the pyraclostrobin particles was less than 2.3 µm.

(c) Into 80 grams of water, 8.2 grams of surfactant 3 and 8.2 grams of surfactant 1 were dissolved then mixed until homogeneous. 0.15 g of defoamer were added. Then 51.9 grams of metconazol was added with stirring and the slurry was milled in a bead mill using 80% loading of 1 mm glass beads until a final particle size of 1.5 µm was achieved (volume average diameter). The suspension was filtered using a 100 mesh sieve to remove unmilled material and chipped beads. This produces a 35% b.w. aqueous suspension of metconazol.

(d) To 217 g of water 15 g of the liquid thickener 2, 0.5 g of defoamer and 31 g of propylene glycol were added and stirred until homogenous. Then 200 g of thickener 3 (1% solution) was added with stirring. Then 390 g of the aqueous pyraclostrobin suspension obtained in step (b) and 146.9 g of the aqueous metconazol suspension obtained in step (c) were added with stirring and stirring was continued until the mixture was homogenous. The thus obtained suspension was filtered using a 100 mesh sieve to remove large material.

The obtained formulation contained 13.6% by weight of pyraclostrobin and 5.1% by weight of metconazol. The viscosity of the formulation was 500 to 1000 cps, determined according to STM-35.0 at 20° C. with 2# spindle. The volume average diameter of the particles was less than 2 µm. The formulation remained stable for more than 3 month at 54° C. with slight increase of particle size. The formulation remained stable for more than 3 month at −10° C. without demixing.

Example 5

Preparation of an Aqueous Suspension Concentrate Containing Pyraclostrobin and Epoxiconazol (a) Into 41.4 grams of water, 4.1 grams of surfactant 4, 2.8 grams of surfactant 5 and 0.1 g of defoamer were added and then mixed until homogeneous. Then 37.2 grams of crystalline pyraclostrobin of modification IV was added and the slurry was milled in a bead mill using 80% loading of 1 mm glass beads until a final particle size of 1.5 µm was achieved (volume average diameter). The suspension was filtered using a 100 mesh sieve to remove unmilled material and chipped beads. This produces a 40% b.w. aqueous suspension where pyraclostrobin is present as its crystalline modification IV.

(b) Into 248 grams of water, 23.5 grams of surfactant 4, 16.0 grams of surfactant 5 and 1.1 g of defoamer were added and then mixed until homogeneous and the mixture was heated to 65-70° C. To this solution 195.8 g of molten pyraclostrobin (70 to 85° C.) were added and the mixture was pumped through a colloid mill, until a pyraclostrobin emulsion of less than 10 microns had been formed. The emulsion was cooled to 40° C. while continuing to pass the mixture through the colloid mill. To this emulsion, 85.6 grams of the aqueous suspension of step (a) was added at 40° C. and the mixture was allowed to continue through the colloid mill for 15 min. The thus obtained suspension was filtered using a 100 mesh sieve to remove large material. The thus obtained suspension contained 40% by weight of pyraclostrobin and the volume average diameter of the pyraclostrobin particles was less than 2.3 µm.

(c) to 570.2 g of the aqueous pyraclostrobin suspension obtained in step (b), 144 g of epoxiconazole and 130.5 g of water were added with stirring and the mixture was passed through a colloid mill for 15 min. at 25° C. Then the mixture was passed twice through a bead mill using 80% loading of 0.6-0.8 mm beads until a final particle size of 2 µm was achieved (volume average diameter). To this suspension 3.4 g of defoamer, 67.6 g of propylene glycol 0.22 g of thickener, 0.18 g of bactericide (Acticide MBS) and 80.3 g of water were added and the mixture was stirred until homogenous.

The obtained formulation contained 22.8% by weight of pyraclostrobin and 14.4% by weight of epoxiconazol. The viscosity of the formulation was 500 to 1000 cps, determined according to STM-35.0 at 20° C. with 2# spindle. The volume average diameter of the particles was less than 2 µm.

Example 6

Preparation of an Aqueous Suspension Concentrate Containing Pyraclostrobin and Fluxapyroxad The following ingredients were added to a suitable vessel with stirring in the following order:

| 1. | 59.0 g | propylene glycol |
| 2. | 18.0 g | Surfactant 2 |
| 3. | 18.0 g | Surfactant 5 |
| 4. | 50.0 g | 18% w/w aqueous solution of surfactant 4 |
| 5. | 410.5 g | demineralized water |

The mixture was heated to 70° C. Then 160.3 g of molten (ca. 75° C.) pyraclostrobin (based on 100% purity) were added under high shear mixing (10000 to 15000 rpm) for about 20 minutes. Subsequently the formed emulsion was cooled down to 40° C. while high shear mixing was still continued. When the temperature of the mixture achieved 40° C., the emulsion was immediately seeded with about 116 g (10% w/w of the total formulation) of the final formulation of a previous run containing pyraclostrobin and fluxapyroxad and having the overall composition given below. Within a few minutes the crystallization started and cooling was continued with high shear mixing until a temperature of 20° C. was achieved. The crystallization was monitored by microscopy. After 30 minutes a particles size distribution of $D_{50}$<2 µm and $D_{90}$<20 µm was achieved. Then, 299.7 g of technical fluxapyroxad (based on 100% purity) are added and mixing is continued for additional 30 minutes.

Subsequently the suspension was passed through a suitable bead mill, using glass beads of 0.75 to 1 mm diameter. Milling was finished, when the specified particle size distribution had been achieved.

Finally 2.5 g xanthan gum dissolved in 20 g water and 4 g of propylene glycol were added with stirring until the xanthan gum was dispersed homogeneously. Then, 2 g of Acticide MBS and 5 g of Silicon SRE (defoamer) were with stirring. Stirring was continued for additional 5 minutes.

The resulting formulation had the following composition:
Final Composition:

| Fluxapyroxad | 167 g/l |
| Pyraclostrobin | 333 g/l |
| 1,2-propylene glycol | 70 g/l |
| Acticide MBS | 2 g/l |
| Surfactant 2 | 20 g/l |
| Surfactant 4 | 10 g/l |
| Surfactant 5 | 20 g/l |
| Deafomer | 5 g/l |
| De-mineralized water | ad 1 l |

Example 7

Preparation of an Aqueous Suspension Concentrate Containing Pyraclostrobin (a) Into a reaction vessel containing 60 grams of water, 10.5 grams of surfactant 3, 3.7 grams of surfactant 6, 0.6 g of defoamer and 35.6 g of glycerine were added with stirring and mixture was stirred until homogeneous. Then 60 grams of crystalline pyraclostrobin of modification IV were added and the slurry was milled in a bead mill using 80% loading of 1 mm glass beads until a final particle size of 1.5 μm was achieved (volume average diameter). The suspension was filtered using a 100 mesh sieve to remove unmilled material and chipped beads. Thereby a 35% b.w. aqueous suspension was obteind, where pyraclostrobin was present as its crystalline modification IV.

(b) Into a reaction vessel containing 600 grams of water, 70 grams of surfactant 3, 24.6 grams of surfactant 6 and 4 g of defoamer were added with stirring and mixture was stirred until homogeneous. Then the mixture was heated to 65 to 70° C. To this solution 402 g of molten pyraclostrobin (70 to 85° C.) were added and the mixture was pumped through a colloid mill, until a pyraclostrobin emulsion having a droplet size of less than 10 μm had been formed. The emulsion was cooled to 40° C. while continuing to pass the mixture through the colloid mill. To this emulsion, 110 grams of the aqueous suspension of step (a) was added at 40° C. and the mixture was allowed to continue through the colloid mill for further 15 min. The thus obtained suspension was filtered using a 100 mesh sieve to remove large material. The thus obtained suspension contained 33% by weight of pyraclostrobin and the volume average diameter of the pyraclostrobin particles was less than 2.3 μm. The suspension remained stable for several month without coarsening.

I claim:

1. A process for preparing an aqueous suspension of an organic pesticide compound, which has a solubility in water of not more than 2 g/l at 20° C. and a melting point of not more than 110° C. and which is capable of forming at least one crystalline form, wherein the organic pesticide compound is present in the form of essentially crystalline particles and wherein at least 90% of the pesticide compound, which is present in the aqueous suspension, is in the crystalline state, which process comprises:
  a) providing an aqueous emulsion of the organic pesticide compound, wherein the organic pesticide compound is present in the form of droplets of an amorphous form of the organic pesticide compound, where the concentration of the organic pesticide compound in the aqueous emulsion is from 10 to 50% by weight, and where the amorphous form is a melt, a supercooled melt or a solid amorphous form, and
  b) adding an aqueous suspension of said organic pesticide compound, wherein the organic pesticide compound is present in the form of essentially crystalline particles and wherein at least 90% of the pesticide compound, which is present in the aqueous suspension, is in the crystalline state,
wherein the addition in step b) is performed at a temperature below the melting temperature of the crystalline form of the organic pesticide compound and where the relative amounts of the aqueous suspension, which is added in step b), and the aqueous emulsion are chosen such that the amount of the organic pesticide compound contained in the aqueous suspension is from 0.01 to 0.3 part by weight, per 1 part by weight of the pesticide compound contained in the aqueous emulsion.

2. The process according to claim 1, wherein the organic pesticide compound is selected from the group consisting of aldrin, alachlor, azinphos-ethyl, benfluralin, bensultap, benzoximate, bifenthrin, binapacryl, bromophos, bromopropylate, butralin, chlorphoxim, chlorpyriphos, fluchloralin, fluoroxypyr, kresoxim-methyl, linuron, metazachlor, metconazol, monolinuron, nitrothal-isopropyl, pendimethalin, phosmet, picoxystrobin, pirimicarb, picolinafen, pyrachlostrobin, tefluthrin, trifloxystrobin and napropamide.

3. The process according to claim 1, where the organic pesticide compound is pyraclostrobin.

4. The process according to claim 3, where in step b) an aqueous suspension of pyraclostrobin is added and where pyraclostrobin is essentially present in the form of its crystalline modification IV.

5. The process according to claim 1, where the addition is performed at a temperature of 10 to 60 K below the melting point of the crystalline form of the organic pesticide compound.

6. The process according to claim 1, where the volume average droplet size of the organic pesticide compound droplets in the aqueous emulsion is from 0.5 to 10 μm.

7. The process according to claim 1, where the concentration of the organic pesticide compound in the aqueous suspension, which is added in step b), is from 1 to 60% by weight.

8. The process according to claim 1, where the volume average particle size of the organic pesticide compound particles in the aqueous suspension, which is added in step b), is from 0.2 to 10 μm.

9. The process according to claim 1, where the aqueous emulsion additionally contains at least one anionic or nonionic polymeric surfactant having at least one polyether group.

10. The process according to claim 9, where the anionic polymeric surfactant is a polymer having a carbon backbone carrying carboxylate groups and polyether side chains.

11. The process according to claim 1, where the aqueous emulsion additionally contains at least one anionic polymeric surfactant having polyether side chains.

12. The process according to claim 11, where the aqueous emulsion additionally contains at least one nonionic surfactant having at least one polyether group.

13. The process according to claim 1, wherein step a) comprises
  a.1) providing an aqueous emulsion of the organic pesticide compound at a temperature where the organic pesticide compound remains in the form of droplets in a molten state, and
  a.2) optionally cooling the aqueous emulsion of the organic pesticide compound to a temperature at least 10 K below the melting point of the crystalline form of the organic pesticide compound.

14. The process according to claim 13, where step a.1) includes providing a melt of the organic pesticide compound and emulsifying the melt in water at a temperature where the organic pesticide compound remains in a molten state.

15. A process for preparing an aqueous pesticide formulation in the form of an aqueous suspension concentrate containing at least one organic pesticide compound, which has a solubility in water of not more than 2 g/l at 20° C. and a melting point of not more than 110° C. and which is capable of forming at least one crystalline form, which process comprises the preparation of an aqueous suspension of the organic pesticide compound, wherein the organic pesticide compound is present in the form of essentially crystalline particles and wherein at least 90% of the pesticide compound, which is present in the aqueous suspension, is in the crystalline state, by a process according to claim 1, which process further comprises adding at least one formulation additive to the aqueous suspension of the organic pesticide compound.

16. The process according to claim 15, wherein the formulation additive is selected from the group consisting of antifreeze agents, viscosity-modifying agents, antifoams, bactericides and coloring agents.

17. The process according to claim 15, which further comprises the addition of at least one further organic pesticide compound.

18. The process according to claim 17, wherein the further organic pesticide compound has a solubility in water of not more than 2 g/l at 20° C.

19. The process according to claim 18, wherein the further organic pesticide compound is selected from the group consisting of metconazol, epoxiconazol, triticonazol, fluquinconazol, prothioconazol, difenoconazol, cyproconazol, carboxin, oxycarboxin, boscalid, isopyrazam, bixafen, penflufen, penthiopyrad, sedaxane, isothianil, N-(3',4',5'-trifluorobiphenyl-2-yl)-1-methyl-3-difluoromethyl-1H-pyrazole-4-carboxamid, N-(4'-trifluoromethylthiobiphenyl-2-yl)-1-methyl-3-difluoromethyl-1H-pyrazole-4-carboxamid, dithianon, pyrimethanil, metiram, mancozeb, captan, folpet, chlorothalonil, thiophanat-methyl, fipronil, teflubenzuron, α-cypermethtrin, clothianidin, thiamethoxam, imidacloprid, abamectin, chlorantraniliprole, metaflumizone, glyphosate, glufosinate, imazomox, imazapyr, imazapic, imazethapyr, dicamba, mepiquat and chlrometquat and, salts of the aforementioned compounds.

20. The process according to claim 18, wherein the further organic pesticide compound is added in the form of an aqueous suspension.

\* \* \* \* \*